(12) United States Patent
Louie (10) Patent No.: US 11,430,554 B2
(45) Date of Patent: Aug. 30, 2022

(54) PHARMACY STOCK SUPPLY TRACKING SYSTEM

(71) Applicant: GSL Solutions, Inc., Vanvouver, WA (US)

(72) Inventor: Shelton Louie, Vancouver, WA (US)

(73) Assignee: GSL SOLUTIONS, INC., Vancouver, WA (US)

( * ) Notice: Subject to any disclaimer, the term of this patent is extended or adjusted under 35 U.S.C. 154(b) by 0 days.

(21) Appl. No.: 16/809,574

(22) Filed: Mar. 5, 2020

(65) Prior Publication Data
US 2021/0043290 A1 Feb. 11, 2021

Related U.S. Application Data

(63) Continuation of application No. 15/331,863, filed on Oct. 22, 2016, now Pat. No. 11,244,747, which is a
(Continued)

(51) Int. Cl.
*G16H 20/10* (2018.01)
*G06Q 10/08* (2012.01)
(Continued)

(52) U.S. Cl.
CPC ........... *G16H 20/10* (2018.01); *G06Q 10/083* (2013.01); *G06Q 10/087* (2013.01); *G16H 20/13* (2018.01); *B65B 57/10* (2013.01); *B65B 57/18* (2013.01)

(58) Field of Classification Search
CPC ...... G16H 20/10; G16H 20/13; G06Q 10/083; G06Q 10/087; B65B 57/18; B65B 57/10
See application file for complete search history.

(56) References Cited

U.S. PATENT DOCUMENTS

| 404,458 A | 6/1889 | Woodruff |
| 541,111 A | 6/1895 | McDonald |

(Continued)

FOREIGN PATENT DOCUMENTS

| EP | 0899677 | 3/1999 |
| EP | 1049042 | 11/2000 |

(Continued)

OTHER PUBLICATIONS

Advisory Action dated May 13, 2010, U.S. Appl. No. 12/268,389, filed Nov. 10, 2008.
(Continued)

*Primary Examiner* — Eliza A Lam
(74) *Attorney, Agent, or Firm* — Morgan, Lewis & Bockius, LLP (57) ABSTRACT

An automated tracking system for a pharmacy that tracks unique identifiers ("UI") with a stock supply of an item or items within a supply container and that provides a security system for determining a discrepancy associated with the stock supply. The UI information automatically travels with the stock supply until it is dispensed to a customer or patient, thereby allowing the system to monitor and track supply for replenishment of the supply or improper or potentially fraudulent transactions. If desired, the improved security allows supply containers and individual supplies within those containers to be stored in the same storage area thereby maximizing available storage space while still improving dispensing and filling accuracy and minimizing loss.

20 Claims, 7 Drawing Sheets

Related U.S. Application Data continuation-in-part of application No. 14/885,960, filed on Oct. 16, 2015, now abandoned, application No. 16/809,574, which is a continuation-in-part of application No. 14/727,584, filed on Jun. 1, 2015, now abandoned, application No. 16/809,574, which is a continuation-in-part of application No. 14/082,607, filed on Nov. 18, 2013, now abandoned, said application No. 14/727,584 is a continuation-in-part of application No. 13/931,012, filed on Jun. 28, 2013, now Pat. No. 9,047,992, said application No. 14/082,607 is a continuation-in-part of application No. 13/282,196, filed on Oct. 26, 2011, now Pat. No. 8,584,941, which is a continuation of application No. 13/050,308, filed on Mar. 17, 2011, now Pat. No. 8,479,988, said application No. 13/931,012 is a continuation of application No. 13/027,075, filed on Feb. 14, 2011, now Pat. No. 8,474,716, said application No. 13/050,308 is a continuation-in-part of application No. 13/027,075, filed on Feb. 14, 2011, now Pat. No. 8,474,716.

(60) Provisional application No. 62/064,911, filed on Oct. 16, 2014, provisional application No. 61/444,062, filed on Feb. 17, 2011.

(51) Int. Cl.
*G16H 20/13* (2018.01)
*B65B 57/10* (2006.01)
*B65B 57/18* (2006.01)

(56) References Cited

U.S. PATENT DOCUMENTS

| | | |
|---|---|---|
| 827,649 A | 7/1906 | Murphy |
| 1,236,324 A | 8/1917 | Leonard |
| 1,592,497 A | 7/1926 | Mays |
| 1,750,291 A | 3/1930 | Whetstone |
| 1,993,477 A | 3/1935 | Glenn et al. |
| 2,174,068 A | 9/1939 | Citron |
| 2,962,335 A | 11/1960 | Benson |
| 3,167,873 A | 2/1965 | Toms |
| 3,172,711 A | 3/1965 | Gillotte |
| 3,744,867 A | 7/1973 | Shaw |
| 3,798,810 A | 3/1974 | Brisson et al. |
| 3,844,416 A | 10/1974 | Potter |
| 3,865,447 A | 2/1975 | Patterson |
| 3,942,851 A | 3/1976 | Kaplan |
| 3,970,010 A | 7/1976 | Cantley |
| 4,019,793 A | 4/1977 | Gerding |
| 4,210,802 A | 7/1980 | Sakai |
| 4,653,818 A | 3/1987 | DeBruyn |
| 4,688,026 A | 8/1987 | Scribner et al. |
| 4,737,910 A | 4/1988 | Kimbrow |
| 4,746,830 A | 5/1988 | Holland |
| 4,766,542 A | 8/1988 | Pilarczyk |
| 4,785,969 A | 11/1988 | McLaughlin |
| 4,793,495 A | 12/1988 | Preu |
| 4,847,764 A | 7/1989 | Halvorson |
| 4,862,160 A | 8/1989 | Ekchian et al. |
| 4,993,558 A | 2/1991 | Assael |
| 5,047,948 A | 9/1991 | Turner |
| 5,079,006 A | 1/1992 | Urquhart |
| 5,160,048 A | 11/1992 | Leyden et al. |
| 5,208,762 A | 5/1993 | Charhut et al. |
| 5,231,273 A | 7/1993 | Caswell et al. |
| 5,245,163 A | 9/1993 | Bar-Yehuda |
| 5,328,784 A | 7/1994 | Fukuda |
| 5,346,297 A | 9/1994 | Colson et al. |
| 5,389,919 A | 2/1995 | Warren et al. |
| 5,434,775 A | 7/1995 | Sims et al. |
| 5,481,546 A | 1/1996 | Dinkins |
| 5,495,250 A | 2/1996 | Ghaem et al. |
| 5,593,267 A | 1/1997 | McDonald et al. |
| 5,595,356 A | 1/1997 | Kewin |
| 5,597,995 A | 1/1997 | Williams et al. |
| 5,640,002 A | 6/1997 | Ruppert et al. |
| 5,646,389 A | 7/1997 | Bravman et al. |
| 5,646,592 A | 7/1997 | Tuttle |
| 5,689,238 A | 11/1997 | Cannon et al. |
| 5,700,998 A | 12/1997 | Palti |
| 5,771,657 A | 6/1998 | Lasher et al. |
| 5,794,213 A | 8/1998 | Markman |
| 5,797,515 A | 8/1998 | Liff et al. |
| 5,798,693 A | 8/1998 | Engellenner |
| 5,801,628 A | 9/1998 | Maloney |
| 5,805,456 A | 9/1998 | Higham et al. |
| 5,838,253 A | 11/1998 | Wurz et al. |
| 5,845,264 A | 12/1998 | Nellhaus |
| 5,907,493 A | 5/1999 | Boyer et al. |
| 5,926,093 A | 7/1999 | Bowers et al. |
| 5,936,527 A | 8/1999 | Isaacman et al. |
| 5,963,132 A | 10/1999 | Yoakum |
| 5,974,393 A | 10/1999 | McCullough et al. |
| 5,996,889 A | 12/1999 | Fuchs et al. |
| 6,008,727 A | 12/1999 | Want et al. |
| 6,021,392 A | 2/2000 | Lester et al. |
| 6,057,756 A | 5/2000 | Engellenner |
| 6,057,764 A | 5/2000 | Williams |
| 6,098,892 A | 8/2000 | Peoples |
| 6,116,505 A | 9/2000 | Withrow |
| 6,150,942 A | 11/2000 | O'Brien |
| 6,155,485 A | 12/2000 | Coughlin |
| 6,170,746 B1 | 1/2001 | Brook et al. |
| 6,202,923 B1 | 3/2001 | Boyer et al. |
| 6,209,978 B1 | 4/2001 | Khan |
| 6,219,587 B1 | 4/2001 | Ahlin et al. |
| 6,223,137 B1 | 4/2001 | McCay et al. |
| 6,232,876 B1 | 5/2001 | Maloney |
| 6,245,057 B1 | 6/2001 | Sieben et al. |
| 6,249,212 B1 | 6/2001 | Boyer et al. |
| 6,259,654 B1 | 7/2001 | de la Huerga |
| 6,294,999 B1 | 9/2001 | Yann et al. |
| 6,318,536 B1 | 11/2001 | Korman et al. |
| 6,324,522 B2 | 11/2001 | Peterson et al. |
| 6,339,732 B1 | 1/2002 | Phoon et al. |
| 6,352,163 B1 | 3/2002 | Barrett et al. |
| 6,354,493 B1 | 3/2002 | Mon |
| 6,357,662 B1 | 3/2002 | Helton et al. |
| 6,366,206 B1 | 4/2002 | Ishikawa et al. |
| 6,366,220 B1 | 4/2002 | Elliott |
| 6,371,311 B1 | 4/2002 | Barrett et al. |
| 6,380,858 B1 | 4/2002 | Yarin et al. |
| 6,392,544 B1 | 5/2002 | Collins et al. |
| 6,393,339 B1 | 5/2002 | Yeadon |
| 6,415,295 B1 | 7/2002 | Feinberg |
| 6,415,978 B1 | 7/2002 | McAllister |
| 6,430,268 B1 | 8/2002 | Petite |
| 6,440,069 B1 | 8/2002 | Raymond et al. |
| 6,448,886 B2 | 9/2002 | Garber et al. |
| 6,450,406 B2 | 9/2002 | Brown |
| 6,464,142 B1 | 10/2002 | Denenberg et al. |
| 6,496,806 B1 | 12/2002 | Horwitz et al. |
| 6,502,005 B1 | 12/2002 | Wrubel et al. |
| 6,522,945 B2 | 2/2003 | Sleep et al. |
| 6,529,786 B1 | 3/2003 | Sim |
| 6,557,758 B1 | 5/2003 | Monico |
| 6,564,121 B1 | 5/2003 | Wallace et al. |
| 6,607,790 B1 | 8/2003 | Musaka |
| 6,611,806 B1 | 8/2003 | Harvey |
| 6,626,302 B2 | 9/2003 | Barrett et al. |
| 6,648,153 B2 | 11/2003 | Holmes |
| 6,693,512 B1 | 2/2004 | Frecska et al. |
| 6,714,121 B1 | 3/2004 | Moore |
| 6,726,232 B2 | 4/2004 | Murphy |
| 6,754,637 B1 * | 6/2004 | Stenz ............... G06Q 10/0837 705/26.1 |
| 6,758,403 B1 | 7/2004 | Keys et al. |
| 6,763,996 B2 | 7/2004 | Rakers et al. |
| 6,769,228 B1 | 8/2004 | Mahar |
| 6,874,684 B1 | 4/2005 | Denenberg et al. |

(56) References Cited

U.S. PATENT DOCUMENTS

| | | | |
|---|---|---|---|
| 6,877,658 | B2 | 4/2005 | Raistrick et al. |
| 6,935,560 | B2 | 8/2005 | Andreasson et al. |
| 6,995,675 | B2 | 2/2006 | Curkendall et al. |
| 7,093,755 | B2 | 8/2006 | Jordan et al. |
| 7,142,118 | B2 | 11/2006 | Hamilton et al. |
| 7,148,803 | B2 | 12/2006 | Bandy et al. |
| 7,158,030 | B2 | 1/2007 | Chung |
| 7,175,081 | B2 | 2/2007 | Andreasson et al. |
| 7,182,256 | B2 | 2/2007 | Andreasson et al. |
| 7,194,333 | B2 | 3/2007 | Shoenfeld |
| 7,216,802 | B1 | 5/2007 | De La Huerga |
| 7,289,015 | B2 | 10/2007 | Moyer |
| 7,382,263 | B2 | 6/2008 | Danowski et al. |
| 7,410,098 | B2 | 8/2008 | Denenberg et al. |
| 7,537,155 | B2 | 5/2009 | Denenberg et al. |
| 7,672,859 | B1 | 3/2010 | Louie et al. |
| 7,787,986 | B2 * | 8/2010 | Pinney ............... G07F 11/60 700/232 |
| 7,813,939 | B2 | 10/2010 | Clements et al. |
| 7,860,603 | B2 | 12/2010 | Handfield et al. |
| 7,887,146 | B1 | 2/2011 | Louie et al. |
| 8,355,962 | B2 | 1/2013 | Delaney et al. |
| 8,380,535 | B2 | 2/2013 | Denenberg et al. |
| 8,474,716 | B2 | 7/2013 | Louie et al. |
| 9,047,992 | B2 | 6/2015 | Louie et al. |
| 2001/0017817 | A1 | 8/2001 | de la Huerga |
| 2001/0040512 | A1 | 11/2001 | Hines et al. |
| 2002/0077857 | A1 * | 6/2002 | Seelinger ............ G16H 40/67 705/2 |
| 2002/0132226 | A1 | 9/2002 | Nair et al. |
| 2002/0180588 | A1 | 12/2002 | Erickson et al. |
| 2003/0050731 | A1 | 3/2003 | Rosenblum |
| 2003/0086338 | A1 | 5/2003 | Sastry et al. |
| 2003/0191430 | A1 | 10/2003 | D'Andrea et al. |
| 2003/0200726 | A1 | 10/2003 | Rast |
| 2004/0036623 | A1 | 2/2004 | Chung |
| 2004/0138921 | A1 * | 7/2004 | Broussard ............ G16H 20/13 705/2 |
| 2204/0167465 | | 8/2004 | Mihai |
| 2005/0049746 | A1 | 3/2005 | Rosenblum |
| 2005/0083213 | A1 | 4/2005 | Stevens et al. |
| 2005/0237201 | A1 | 10/2005 | Nedblake |
| 2006/0089858 | A1 | 4/2006 | Ling |
| 2006/0190628 | A1 | 8/2006 | Linton et al. |
| 2006/0224414 | A1 | 10/2006 | Astrup et al. |
| 2008/0222042 | A1 | 9/2008 | Moore et al. |
| 2009/0321470 | A1 | 12/2009 | Knoth |
| 2010/0059585 | A1 | 3/2010 | Fellows et al. |
| 2010/0268548 | A1 * | 10/2010 | Louie ................. G07G 1/0036 705/2 |
| 2010/0283601 | A1 | 11/2010 | Tai |
| 2011/0146835 | A1 | 6/2011 | Terzini |
| 2012/0209422 | A1 | 8/2012 | Wagner |
| 2013/0035950 | A1 * | 2/2013 | MacDonald ......... G16H 40/63 705/2 |

FOREIGN PATENT DOCUMENTS

| | | |
|---|---|---|
| WO | WO-2006084310 | 8/2006 |
| WO | WO-2008006203 | 1/2008 |
| WO | WO-2013082392 A1 | 6/2013 |

OTHER PUBLICATIONS

Derfler, Frank J. et al., How Networks Work, Millenium Ed., Que Corporation, Aug. 23, 2000.
Final Office action dated Apr. 25, 2007, U.S. Appl. No. 10/223,336, filed Aug. 18, 2002.
Final Office action dated Aug. 25, 2006, U.S. Appl. No. 10/223,308, filed Aug. 18, 2002.
Final Office action dated Dec. 10, 2013, U.S. Appl. No. 12/715,256, filed Mar. 1, 2010.
Final Office action dated Dec. 24, 2008, U.S. Appl. No. 10/223,308, filed Aug. 18, 2002.
Final Office action dated Dec. 28, 2005, U.S. Appl. No. 09/829,536, filed Apr. 9, 2001.
Final Office action dated Dec. 4, 2007, U.S. Appl. No. 09/829,536, filed Apr. 9, 2001.
Final Office action dated Feb. 15, 2012, U.S. Appl. No. 12/715,256, filed Mar. 1, 2010.
Final Office action dated Feb. 21, 2007, U.S. Appl. No. 09/991,529, filed Nov. 16, 2001.
Final Office action dated Feb. 23, 2005, U.S. Appl. No. 09/991,530, filed Aug. 18, 2002.
Final Office action dated Jul. 16, 2004, U.S. Appl. No. 09/829,536, filed Apr. 9, 2001.
Final Office action dated Jun. 15, 2007, U.S. Appl. No. 09/715,439, filed Nov. 16, 2000.
Final Office action dated Jun. 18, 2009, U.S. Appl. No. 10/928,756, filed Aug. 26, 2004.
Final Office action dated Jun. 23, 2005, U.S. Appl. No. 10/223,336, filed Aug. 18, 2002.
Final Office action dated Mar. 16, 2010, U.S. Appl. No. 10/928,758, filed Aug. 26, 2004.
Final Office action dated Mar. 22, 2012, U.S. Appl. No. 12/825,020, filed Jun. 28, 2010.
Final Office action dated Mar. 25, 2013, U.S. Appl. No. 13/027,075, filed Feb. 14, 2011.
Final Office action dated May 15, 2003, U.S. Appl. No. 09/715,439, filed Nov. 16, 2000.
Final Office action dated May 17, 2006, U.S. Appl. No. 09/991,249, filed Nov. 16, 2001.
Final Office action dated Oct. 4, 2010, U.S. Appl. No. 12/268,389, filed Nov. 10, 2008.
Final Office action dated Oct. 8, 2004, U.S. Appl. No. 10/223,308, filed Aug. 18, 2002.
Final Office action dated Sep. 21, 2005, U.S. Appl. No. 09/715,439, filed Nov. 16, 2000.
Final Office action dated Sep. 23, 2013, U.S. Appl. No. 13/550,577, filed Jul. 16, 2012.
Final Office action dated Sep. 4, 2008, U.S. Appl. No. 09/715,439, filed Nov. 16, 2000.
Gralla, Preston, How the Internet Works, Millenium Ed., Que Corporation, Sep. 23, 1999.
Office action dated Mar. 19, 2015, U.S. Appl. No. 12/715,256, filed Mar. 1, 2010.
Office action dated Apr. 19, 2007, U.S. Appl. No. 09/829,536, filed Apr. 9, 2001.
Office action dated Apr. 28, 2004, U.S. Appl. No. 09/991,249, filed Nov. 16, 2001.
Office action dated Apr. 4, 2007, U.S. Appl. No. 11/213,321, filed Aug. 25, 2005.
Office action dated Apr. 8, 2005, U.S. Appl. No. 09/829,536, filed Apr. 9, 2001.
Office action dated Aug. 1, 2011, U.S. Appl. No. 12/715,256, filed Mar. 1, 2010.
Office action dated Aug. 15, 2006, U.S. Appl. No. 10/223,336, filed Aug. 18, 2002.
Office action dated Aug. 29, 2012, U.S. Appl. No. 13/027,075, filed Feb. 14, 2011.
Office action dated Aug. 7, 2008, U.S. Appl. No. 10/928,756, filed Aug. 26, 2004.
Office action dated Dec. 17, 2007, U.S. Appl. No. 11/213,321, filed Aug. 25, 2005.
Office action dated Dec. 2, 2005, U.S. Appl. No. 10/223,308, filed Aug. 18, 2002.
Office action dated Dec. 23, 2003, U.S. Appl. No. 10/223,308, filed Aug. 18, 2002.
Office action dated Feb. 15, 2012, U.S. Appl. No. 12/715,256, filed Mar. 1, 2010.
Office action dated Feb. 28, 2013, U.S. Appl. No. 13/550,577, filed Jul. 16, 2012.
Office action dated Jan. 10, 2014, U.S. Appl. No. 12/825,020, filed Jun. 28, 2010.

(56) References Cited

OTHER PUBLICATIONS

Office action dated Jan. 12, 2005, U.S. Appl. No. 09/715,439, filed Nov. 16, 2000.
Office action dated Jan. 14, 2008 U.S. Appl. No. 10/928,717, filed Aug. 26, 2004.
Office action dated Jan. 19, 2010, U.S. Appl. No. 12/268,389, filed Nov. 10, 2008.
Office action dated Jun. 11, 2009, U.S. Appl. No. 09/715,439, filed Nov. 16, 2000.
Office action dated Jun. 9, 2011, U.S. Appl. No. 12/825,020, filed Jun. 28, 2010.
Office action dated Mar. 13, 2009 U.S. Appl. No. 10/929,110, filed Aug. 26, 2004.
Office action dated Mar. 2, 2010, U.S. Appl. No. 10/223,308, filed Aug. 18, 2002.
Office action dated Mar. 30, 2004, U.S. Appl. No. 09/715,439, filed Nov. 16, 2000.
Office action dated May 10, 2004, U.S. Appl. No. 09/991,530, filed Aug. 18, 2002.
Office action dated May 12, 2009, U.S. Appl. No. 10/928,758, filed Aug. 26, 2004.
Office action dated May 31, 2013, U.S. Appl. No. 12/715,256, filed Mar. 1, 2010.
Office action dated Nov. 12, 2003, U.S. Appl. No. 09/829,536, filed Apr. 9, 2001.
Office action dated Nov. 2, 2007, U.S. Appl. No. 10/223,308, filed Aug. 18, 2002.
Office action dated Nov. 27, 2007, U.S. Appl. No. 09/715,439, filed Nov. 16, 2000.
Office action dated Nov. 29, 2012, U.S. Appl. No. 13/282,196, filed Oct. 26, 2011.
Office action dated Nov. 6, 2006, U.S. Appl. No. 09/715,439, filed Nov. 16, 2000.
Office action dated Oct. 13, 2004, U.S. Appl. No. 10/223,336, filed Aug. 18, 2002.
Office action dated Oct. 21, 2002, U.S. Appl. No. 09/715,439, filed Nov. 16, 2000.
Office action dated Sep. 5, 2003, U.S. Appl. No. 09/715,439, filed Nov. 16, 2000.
Office action dated Sep. 8, 2004 U.S. Appl. No. 09/991,529, filed Nov. 16, 2001.
U.S. Appl. No. 09/715,439, filed Nov. 16, 2000.
U.S. Appl. No. 09/829,536, filed Apr. 9, 2001.
U.S. Appl. No. 09/991,249, filed Nov. 16, 2001.
U.S. Appl. No. 09/991,529, filed Nov. 16, 2001.
U.S. Appl. No. 09/991,530, filed Nov. 16, 2001.
U.S. Appl. No. 10/223,336, filed Aug. 18, 2002.
U.S. Appl. No. 10/925,221, filed Aug. 23, 2004.
U.S. Appl. No. 10/925,222, filed Aug. 23, 2004.
U.S. Appl. No. 10/925,360, filed Aug. 23, 2004.
U.S. Appl. No. 10/925,373, filed Aug. 23, 2004.
U.S. Appl. No. 10/928,717, filed Aug. 26, 2004.
U.S. Appl. No. 10/928,756, filed Aug. 26, 2004.
U.S. Appl. No. 10/928,758, filed Aug. 26, 2004.
U.S. Appl. No. 10/929,110, filed Aug. 26, 2004.
U.S. Appl. No. 11/213,321, filed Aug. 25, 2005.
U.S. Appl. No. 12/268,389, filed Nov. 10, 2008.
U.S. Appl. No. 12/715,256, filed Mar. 1, 2010.
U.S. Appl. No. 12/825,020, filed Jun. 28, 2010.
U.S. Appl. No. 13/050,308, filed Mar. 17, 2011.
U.S. Appl. No. 13/282,196, filed Oct. 26, 2011.
White, Ron, How Computers Work, Millenium Ed., Que Corporation, Sep. 22, 1999.
International Search Report and Written Opinion for Application No. PCT/US2015/056109, dated Jan. 8, 2016, 6 pages.
International Search Report and Written Opinion for Application No. PCT/US2015/056107, dated Jan. 6, 2016, 7 pages.
Extended European Search Report for Application No. 15851181.6, dated May 4, 2018, 10 pages.
European Summons to attend oral proceedings for Application No. 15851181.6, dated Apr. 8, 2022, 10 pages.

* cited by examiner

PHARMACY STOCK SUPPLY TRACKING SYSTEM

CROSS-REFERENCE TO RELATED APPLICATIONS

This application claims priority to and is a continuation-in-part of U.S. patent application Ser. No. 14/082,607, filed on Nov. 18, 2013 which is a continuation-in-part of U.S. patent application Ser. No. 13/282,196, filed Oct. 26, 2011, now U.S. Pat. No. 8,584,941, which is a continuation of U.S. patent application Ser. No. 13/050,308, filed Mar. 17, 2011, now U.S. Pat. No. 8,479,988, which claims the benefit of 61/444,062, filed Feb. 17, 2011, is a continuation-in-part U.S. patent application Ser. No. 13/027,075, filed Feb. 14, 2011, now U.S. Pat. No. 8,474,716. The entire disclosure of these references is hereby incorporated by reference.

This application also claims priority to and is a continuation-in-part of Ser. No. 14/727,584, filed on Jun. 1, 2015, which is a continuation-in-part of U.S. application Ser. No. 13/931,012, filed on Jun. 28, 2013, now U.S. Pat. No. 9,047,992, issued on Jun. 2, 2015, which is a continuation of U.S. application Ser. No. 13/027,075, filed on Feb. 14, 2011, now U.S. Pat. No. 8,474,716, issued on Jul. 2, 2013. The entire disclosure of these references is hereby incorporated by reference.

This application also claims priority to and is a continuation-in-part of U.S. patent application Ser. No. 15/331,863, filed Oct. 22, 2016, now U.S. Pat. No. 11,244,747, which is a continuation-in-part of U.S. patent application Ser. No. 14/885,960, filed on Oct. 16, 2015, now abandoned, which claims priority to U.S. provisional patent application Ser. No. 62/064,911 filed on Oct. 16, 2014. This entire disclosure of these references is hereby incorporated by reference.

BACKGROUND

Automated systems and methods for monitoring and tracking prescription orders, pharmacy supply containers, filled prescriptions and the like are known. Examples of these systems can be found in U.S. Pat. No. 8,479,988 to Louie, et al., and U.S. Pat. No. 7,747,477 to Louie et al., the disclosures of which are hereby incorporated by reference.

Also, local retail pharmacies, healthcare facilities and the like are increasingly relying on remote, "central fill" pharmacies to fill prescription orders of customers and patients and ship the filled prescriptions to the local retail pharmacy or healthcare facility for dispensing to the customer or patient. An exemplar, remote "central fill" pharmacy system is shown in U.S. Pat. No. 7,448,544 to Louie et al., the disclosure of which is hereby incorporated by reference.

In addition, automated prescription filling machines are known and in common use. These machines automatically count and dispense a desired medication into a container and apply a label containing customer identifying information. Some of these machines include automated verification systems, such as measuring the weight of the filled prescription and comparing it to a predetermined weight and flagging an error if the detected weight differs from the predetermined weight. These systems can also include automated visual detection systems such as cameras or the like that can physically count the number of pills dispensed and the appearance of the pills and compare those detected values with predetermined criteria and flag any discrepancies detected. Exemplar automated filling system are shown in U.S. Pat. No. 8,275,481 to Rice et al., U.S. patent application Ser. No. 13/473,267 to Luciano, et al., and U.S. patent application Ser. No. 13/325,782 to Rhoads, the disclosures of which are hereby incorporated by reference. These automated verification systems have proven themselves to be accurate and reliable.

In general, a licensed pharmacy technician or pharmacist is required to verify that a prescription for a customer has been properly filled. This verification usually includes verifying that the proper medication has been loaded into the correct locations within an automated filling machine, and that the proper amount of that medication has been placed in the container earmarked for the customer/patient, and that the customers/patient's container is properly labeled. Labeling includes identifying information about the medication, quantity, how to take the medication contained therein and the customer/patient it is intended for.

In cases where a prescription order is filled at a remote facility, there may be several licensed pharmacy technicians and/or pharmacists along the filling flow process that perform the same verification steps for the same prescription and supply container orders. While such redundant verification is certainly beneficial in the rare case where verification along the flow process is erroneous, it needlessly increases the workload of the pharmacy technicians/pharmacists. Moreover, it requires more licensed pharmacy technicians & pharmacists to be involved in the filling and dispensing process than needed to accurately and consistently dispense the correct medications to patients and customers. Since the demand on licensed pharmacy technicians and pharmacists is continuing to increase, these redundant verification systems can compromise a pharmacy's ability to timely dispense medications to patients and customers.

Moreover, most medical-related items and medications have Unique Identifiers such as Unique Drug Identity ("UDI") information associated with it including its lot number, expiration date, pedigree code, National Drug Code ("NDC"), Drug Identification Number ("DIN"), cost and pricing information, and the like. This information is provided by the manufacturer of the medical items or medication within the supply container. However, much of this information, and even the fact the item or items have been removed from the container, is lost for when the item is withdrawn from the supply container.

Also, many medications have become increasingly expensive with individual doses of certain medications costing as much as several thousand dollars per dose. The costs to stock such medications have become increasingly burdensome to some pharmacies, and they risk losing their investment in cases where the stocked medication expires before it can be dispensed. As a result, many pharmacies will not stock certain medications, and instead order such medication from the manufacturer as it receives an order for it by customers. This ordering process can take several days before the medication is available to be dispensed to a customer, thereby delaying when a customer can start treatment.

Similarly, given the large number of workers involved in filling and dispensing a prescription order, there is little tracking or accountability of workers who have access to medications contained in supply containers and/or individual filled prescriptions. This lack of accountability can contribute to loss and theft of medications by workers.

Also, should a particular medication be recalled by its manufacturer or for another reason, the process of manually locating unused supplies of the medication within a pharmacy or awaiting customer pickup in a will call area is time consuming, and this process can miss some medications from being timely recalled.

Moreover, known pharmacy storage systems often require that supply containers and individual filled prescriptions awaiting pickup be stored in separate storage areas within a pharmacy, which often already have limited space to accommodate two separate storage areas.

SUMMARY

Thus, despite the known systems for filling prescription orders of customers and patients and filling and loading supply containers containing medications into automated filling machines, there remains a need for a cost effective system that consistently and accurately verifies supplies within supply containers within a pharmacy without needlessly requiring multiple verifications from different workers within the pharmacy.

Moreover, there remains a need for medical item unique identifiers and medication UDI information of a supply to follow the filling flow through a system to each individual items are dispensed to a customer or patient.

In addition, there remains a need for the financial information of a supply of medication to follow the filling flow through a system to each individual filled prescription order of a customer such that financial ownership of a particular customer's supply of medication and that customer's payment for it can pass directly between the manufacturer or a third party owner of the medication and the customer without a dispensing pharmacy being held financially responsible as an "owner" of the supply of medication while under its control.

Also, there remains a need for an automatic fraud detection system that monitors dispensing of medications by each worker compared to a predetermined criteria and alerts management should a discrepancy be detected.

In addition, there remains a need for a reliable and secure storage device that allows supply containers and individual filled prescription orders to both be stored therein while still allowing controlled access and detailed tracking of these items.

The advantages and features of novelty characterizing aspects of the invention are pointed out with particularity in the appended claims. To gain an improved understanding of the advantages and features of novelty, however, reference may be made to the following descriptive matter and accompanying figures that describe and illustrate various configurations and concepts related to the invention.

FIGURE DESCRIPTIONS

The foregoing Summary and the following Detailed Description will be better understood when read in conjunction with the accompanying figures.

DETAILED DESCRIPTION

Figure 1:
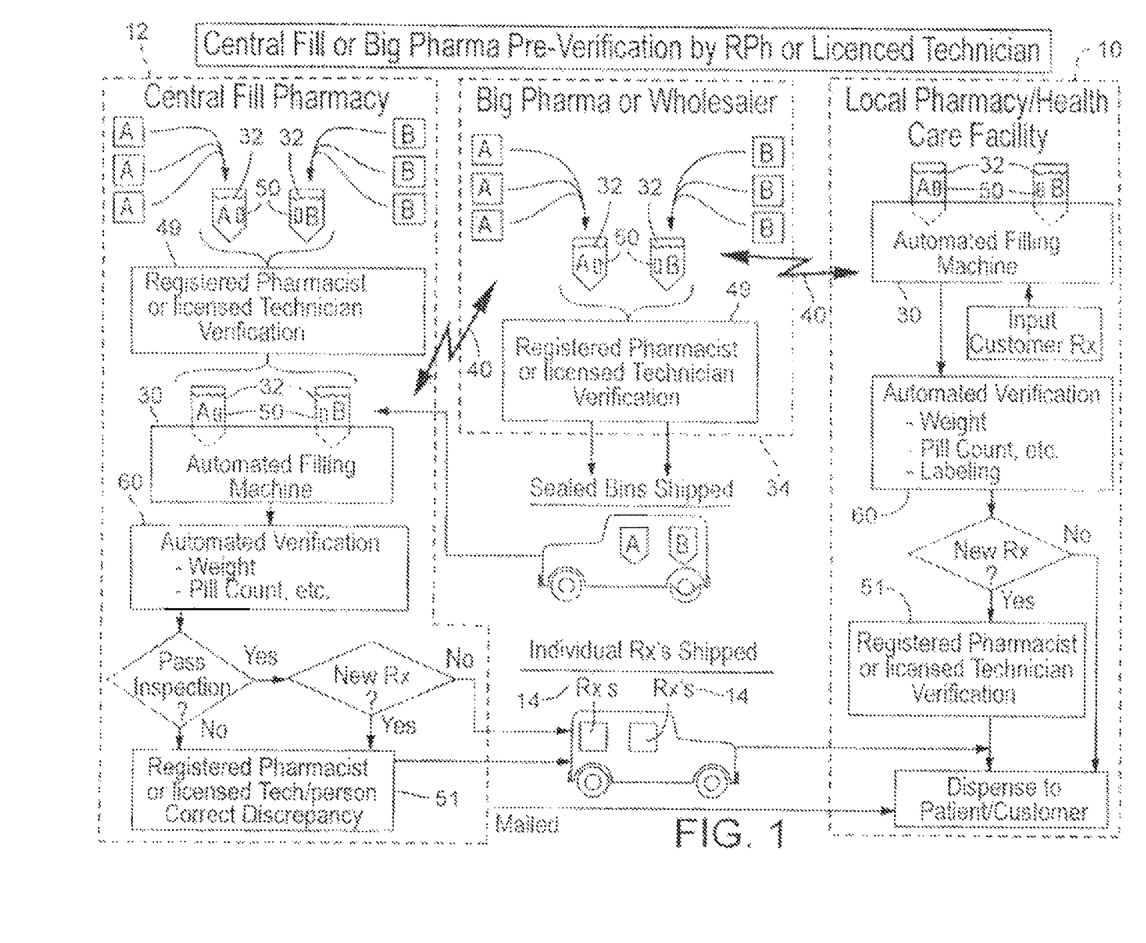
FIG. 1 is flow chart of an exemplar pharmacy filling system that uses a central fill pharmacy to fill the prescription order and a local pharmacy to dispense the prescription order to a customer or patient in accordance with an embodiment of the present invention. The automated filling machine is filled with medications contained in bins that have been filled and verified by a pharmacist or licensed pharmacy technician at a third party location, such as a wholesaler, a pharmaceutical manufacturer, or a central fill location.
Figure 2:
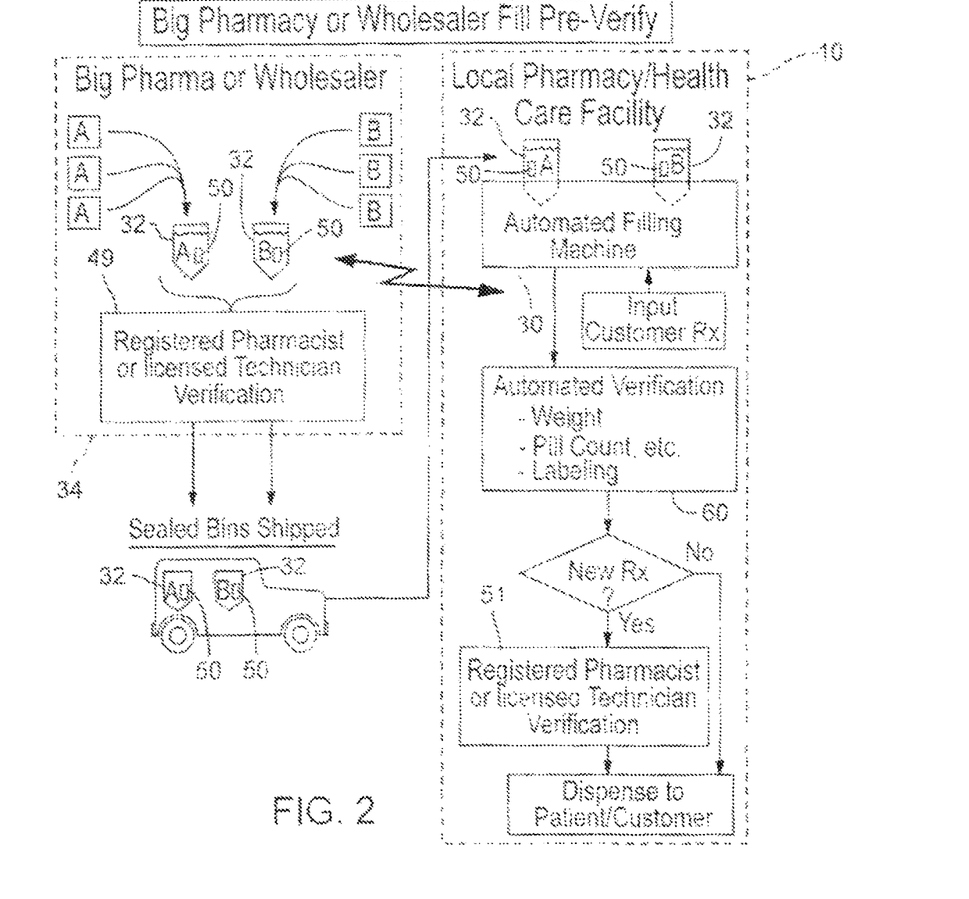
FIG. 2 is a flow chart of an exemplar pharmacy filling system that uses a local pharmacy or healthcare facility to fill the prescription orders by relying on a third party, such as a wholesaler or pharmaceutical manufacturer, to provide bins filled with supply medications that have been filed and verified by a pharmacist or licensed pharmacy technician at the third party location.

A pharmacy filling system is shown in FIGS. 1-7. A local pharmacy 10 or healthcare facility may use a central fill pharmacy 12 to assist with filling an individual prescription order 14 as shown in FIG. 1, or it may fill the prescription order 14 within the local or retail pharmacy 10 itself as shown in FIG. 2. A prescription order 14 is usually a lawful written order prescribed to a patient by a practitioner for the quantity, strength, and dosage instructions of a given medication or device for the treatment of a condition of that patient. A prescription order may also be more broadly defined by a national or local governing authority, and that definition is also hereby included herein.

Figure 3:
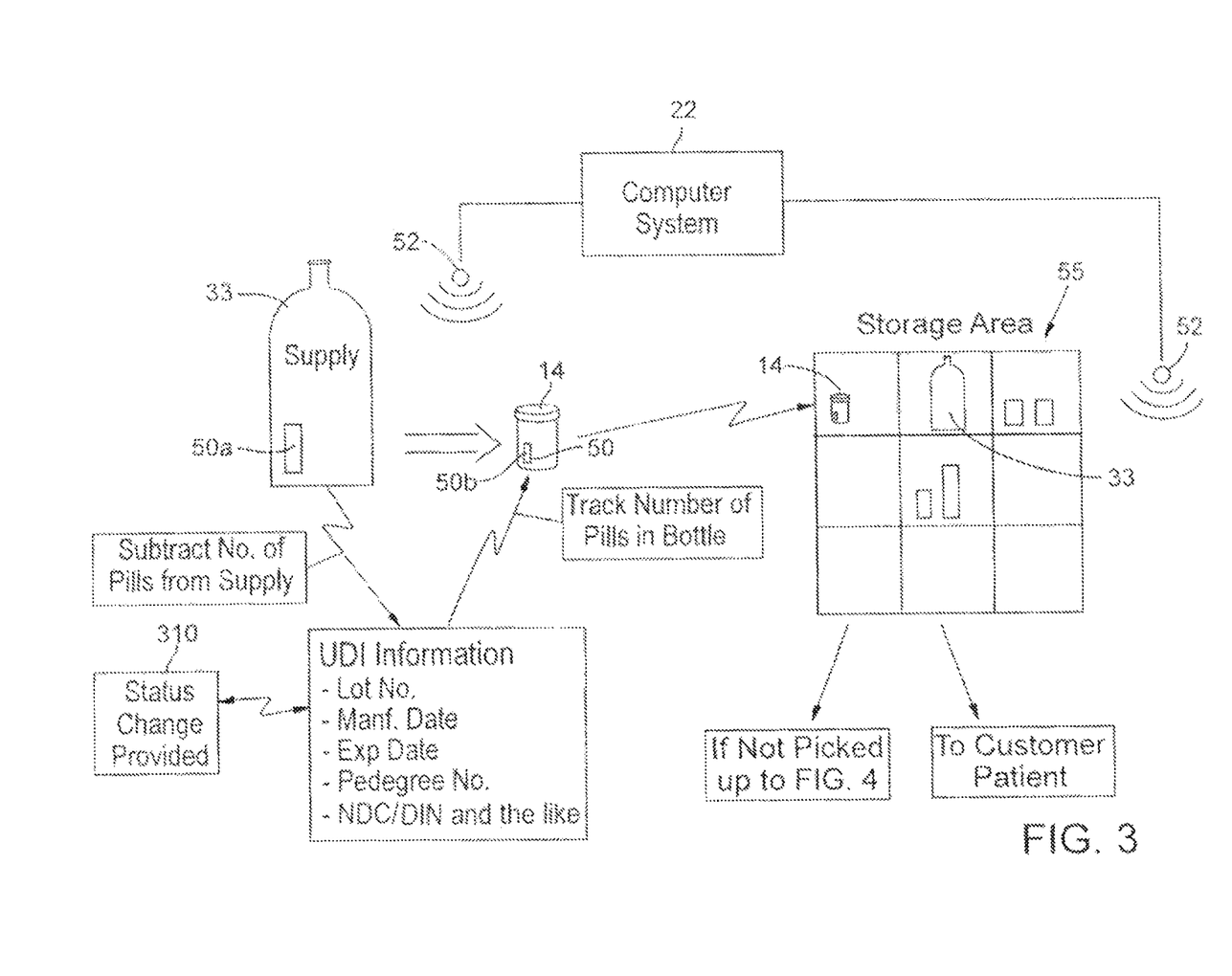
FIG. 3 is a schematic diagram of an exemplar filling of an individual prescription order of a customer from a stock supply of the prescribed medication showing the transfer from Unique Drug Identifier ("UDI") information about the medication in the stock supply container to a computer readable tag that travels with the individual prescription order in accordance with an embodiment of the present invention. In a disclosed embodiment, a computer system uses the tag to track, monitor and locate the individual prescription, correlate it with a customer, and maintain UDI information of the medication contained with the individual prescription.
Figure 4:
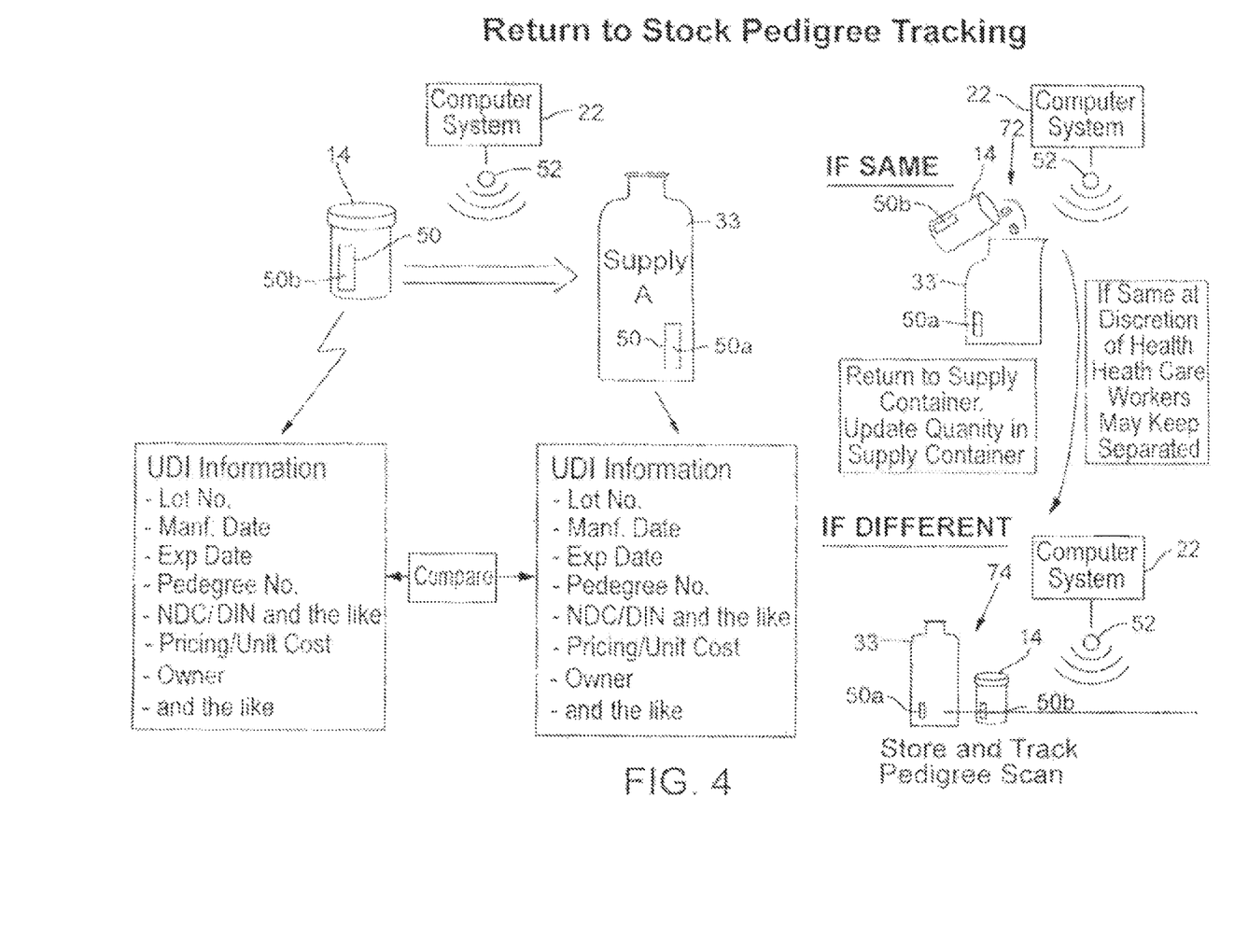
FIG. 4 is a schematic diagram of an exemplar "Return to Stock" comparison whereby the computer system compares the UDI of an individual prescription order that was not timely dispensed to a customer or patient to the UDI of a supply container and authorizes the return of the medication to the stock supply container only if the UDI's between them are identical.
Figure 5:
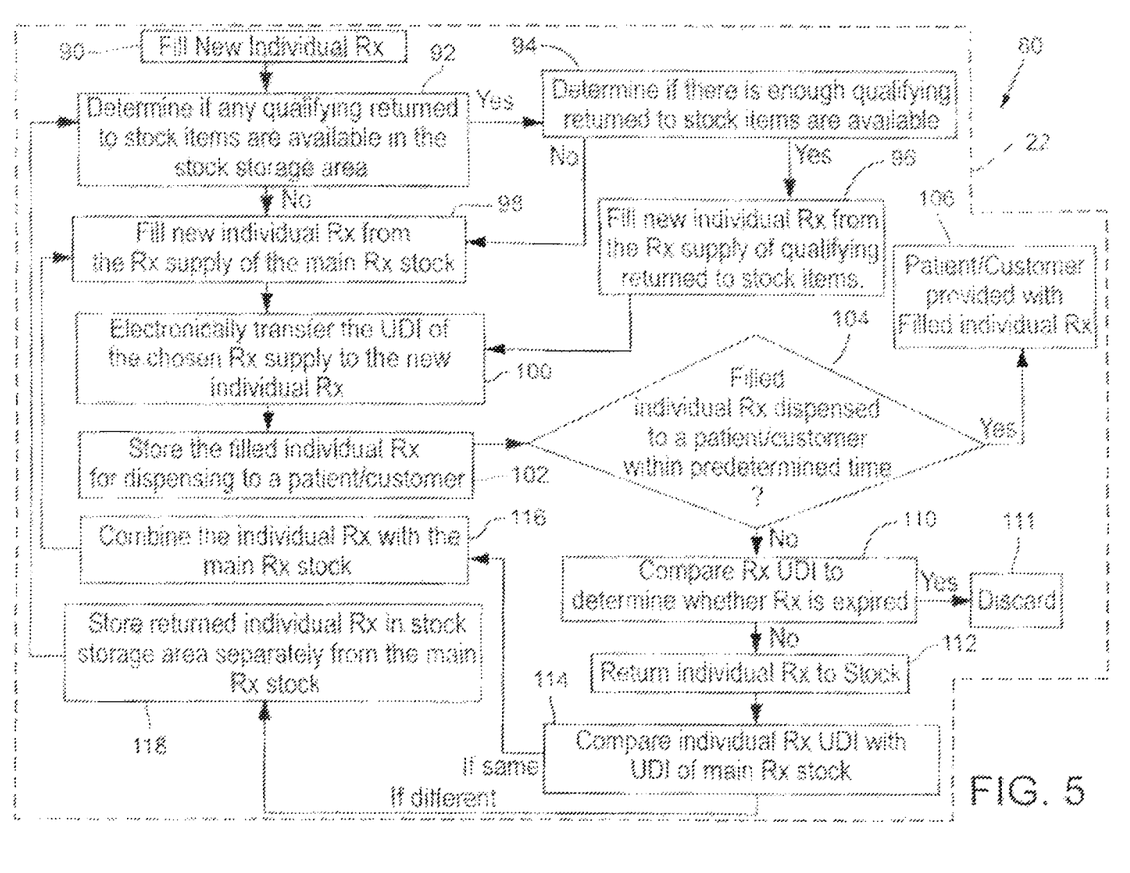
FIG. 5 is a flow chart of an exemplar prescription order filling system with a computer system monitored and verified "return to stock" feature that minimizes medication loss while preserving UDI integrity of the returned to stock medications.
Figure 6:
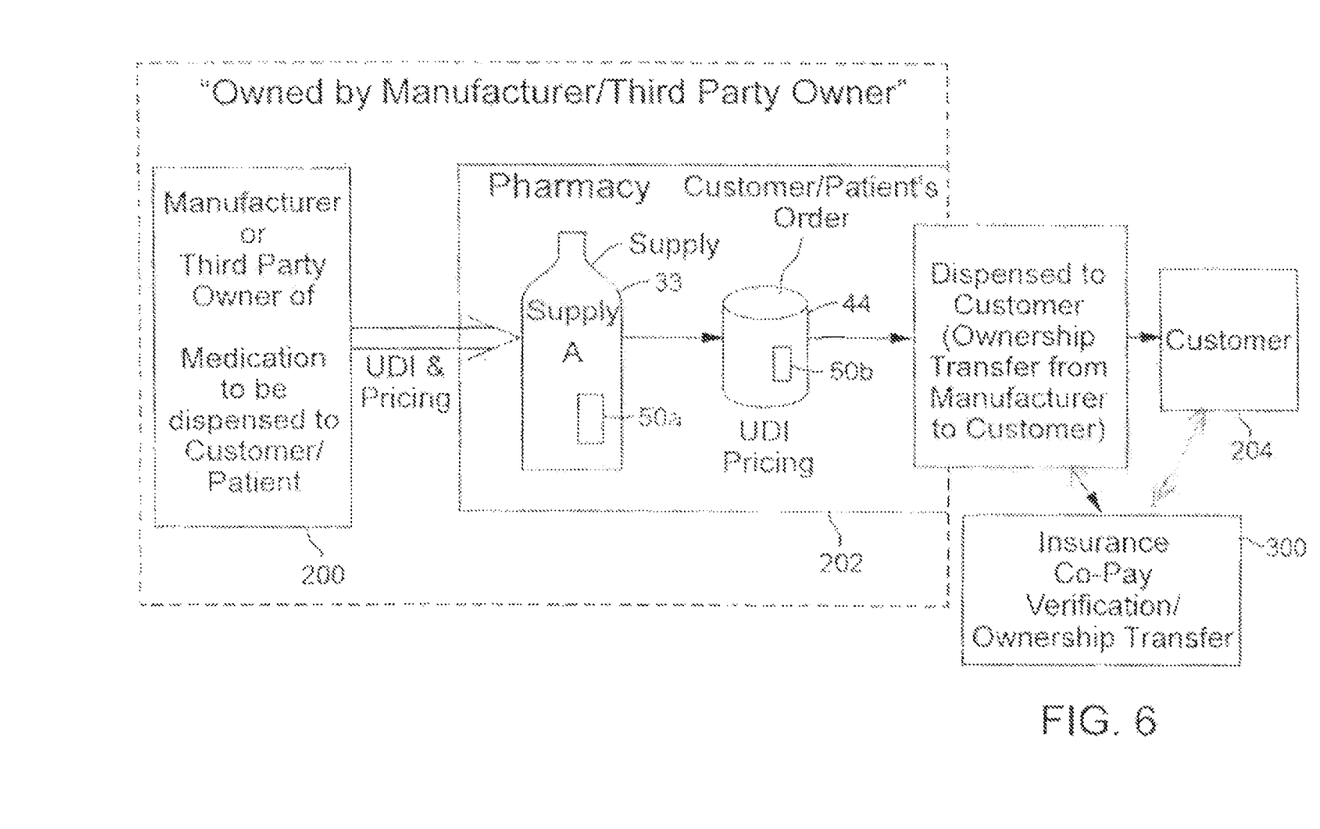
FIG. 6 is a schematic diagram of an exemplar flow path from a manufacturer or third party owner of a medication to a customer/patent that is dispensed to the customer/patient by a pharmacy that maintains a supply of the medication to dispense to the customer/patient, but because of the tracking of UDI, ownership, and pricing tracking by the tracking system, the pharmacy does not purchase or otherwise obtain ownership of the medication from the pharmacy. Ownership passes directly from the manufacturer or third party owner of the medication to the customer/patient.
Figure 7:
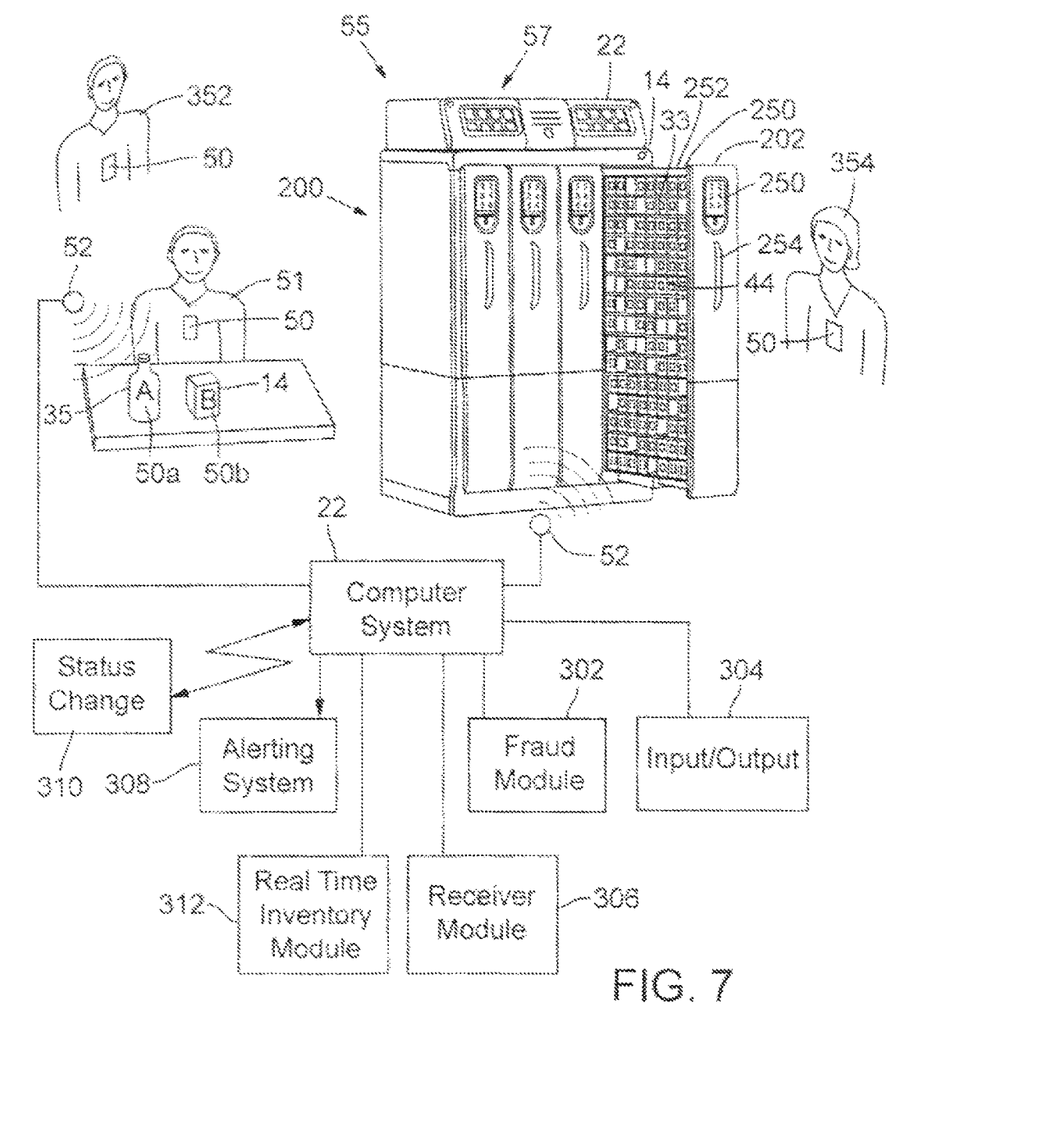
FIG. 7 is a schematic diagram of an exemplar pharmacy system having a dual use storage compartment for securely storing both supply containers and filled prescription orders with security features to monitor and track access to items stored therein and monitor fraudulent dispensing. It also includes security systems such as a system for globally identifying all medications within the pharmacy subject to a status change such as a recall or the like, a real-time inventory module, a fraud module, and a receiver module.

FIGS. 3-5 show an exemplar prescription medication dispensing system 20 to a customer or patent with a computer system 22 monitored and verified "return to stock" feature that minimizes medication loss while preserving the Unique Drug Identifier ("UDI") of medication that is returned to stock. FIG. 6 shows an exemplar use of the dispensing system's UDI, ownership, and pricing tracking to track the passing of ownership of the dispensed medication directly from the manufacturer to a customer/patient without a dispensing pharmacy being financially responsible for the medication while under its control. Each of these features is discussed in greater detail below. FIG. 7 shows possible security features that may be included with the system for ensuring actuate filling and dispensing of prescription orders, minimizing fraud and other losses, and maximizing available storage space.

Automated Prescription Filling with System Tracking and Verification

Regarding FIGS. 1 & 2, in both embodiments, an automated filling machine or system 30 is used to fill the prescription orders 14. The automated filling system 30 is located at the central fill facility 12 in the embodiment of FIG. 1, and at the local pharmacy 10 or healthcare facility in the embodiment in FIG. 2. At either location, the automated filling system 30 is stocked with medication supply bins 32 that have been filled and verified by a pharmacist and/or licensed pharmacy worker 49 at a remote location 34 such as a wholesaler or the medication manufacturer. The local pharmacy 10 or healthcare facility is preferably in electronic or computer communication 40 with the remote location 34 and central fill facility 12, if applicable.

The supply bins 32 are sealed and tagged at the remote location 34, preferably with an electronic tag 50 such as a barcode, RF tag, RFID tag, GPS tag, or the like, that travels with each supply bin 32. The tag 50 includes identifying information about the medication contained within the supply bin 32 to which it is attached. Preferably, the tag 50 is in communication with a computer system 22 that includes one or more tag readers 52 that detect the presence of the tag to determine its location. The computer system 22 includes a database that may include detailed information about the medication contained within the supply bin 32 including its location as well as UDI information about the medication.

More preferably, the tag 50 is a radio-frequency identification tag ("RFID"), and includes Unique Drug Identity ("UDI") information regarding the medication contained within the bin 32. Such information can include the lot number, expiration date, drug name, drug strength, pedigree number, fill date, pharmacist/licensed pharmacy worker verification and identification, current owner, pricing, unit cost, and the like for the medication contained in the bin.

The sealed bins 32 are transported to their respective automated filling system 30, which is either the central fill pharmacy 12 in the embodiment of FIG. 1, or the local pharmacy/health care facility 10 in the embodiment of FIG. 2. A local worker (51, FIG. 7), who may also be tagged with a unique identifier tag 50 so his or her actions within the pharmacy can also be monitored, tracked and recorded by the computer system 22, installs the bins 32 into the automated filling system 30 by breaking the seal. A local tracking system in communication with the computer system 22, such as a system disclosed in U.S. Pat. No. 8,479,988 to Louie, et al. or the like, uses a tag reader 52 or the like to automatically read the information contained on the tag 50 that is operably secured to the bin 32. The computer system 22 automatically verifies that the correct bin 32 has been placed in the correct location within the automated filling system 30 without requiring a local licensed pharmacy worker or pharmacists to verify the contents of the bin 32 or its proper location within the automated filling machine 30.

Should the computer system 22 detect a discrepancy, such as the wrong supply bin 32 being installed in the wrong location, the system 22 can alert a worker to correct the discrepancy or call of a licensed pharmacy worker or pharmacist to intervene to correct the situation.

During filling of the prescription order 14, either at the central fill pharmacy 12 in FIG. 1 or at the local pharmacy 10 or healthcare facility of FIG. 2, the supply bins 32 and the prescription orders 14 are tagged with electronic machine readable tags 50 that monitor and track their location within the pharmacy and include information about the prescription orders and/or supply bin contents (e.g. UDI's) as needed.

The automated filling machine 30 may include standard automated filling verification systems 60 such as weight verification, label verification, pill count verification, video comparison of the pills to an image of the pill in a standard catalog of pills, and the like. These verification systems 60 verify that the automated filling machine 30 property placed the correct medication and the correct amount of that medication into a container that has been properly labeled for a particular customer or patient. Should these systems detect a discrepancy, the system alerts a pharmacy worker of any discrepancies where that particular prescription order 14 is pulled from the system and manually inspected and corrected by a pharmacy worker before it is released to a customer or patient.

It can be appreciated, that with the foregoing systems, individual electronic tagging 50, tracking and monitoring of the supply bins 32 and the prescription orders 14, and automated verifications systems 60 downstream of the filling machines 30, a filled prescription order 14 for a refilled prescription may be dispensed to a customer with only one manual verification of the supply bins 32, by a healthcare worker, well upstream of the individual filling of the prescription 14. The downstream automated monitoring, testing, tracking and verification performed by the computer system 22 maintains the integrity of the supply bins 32 and the resulting filled prescription orders 14.

Of course, the filling system can include additional inspection stations along the filling path as needed to comply with local pharmacy dispensing regulations. For example, if a prescription order 14 is new, and calls for new prescription handling or patient counseling, a registered pharmacy worker and/or pharmacist 51 can be called in to verify that particular order and counsel the customer or patient. Refilled orders can pass this step saving licensed pharmacy worker's and pharmacist's time.

If desired, the pharmacist or licensed pharmacy worker 49 at a remote location 34 and/or the pharmacists or licensed pharmacy worker 51 at the local pharmacy 10 can each wear a tag 50 that is in communication with the computer system 22. This allows for the computer system 22 to monitor, track and document which workers performed which tasks related to both the supply bins 32 and individual prescription orders 14

System Tracking and Verification of Unique Drug Identifier

Referring to FIGS. 3-5, the computer system 22 can monitor and track the Unique Identifier such as a Unique Drug Identifier ("UDI") information about the item or items such as medication in each stock supply container 33 within the system, such as lot number, manufacturer date, expiration date, drug name, drug strength, pedigree number, National Drug Code ("NDC"), Drug Identification Number ("DIN"), cost and pricing information, and the like. The supply container 33 may be from a previously packaged bin 32 or a separate container that arrived at the pharmacy by other methods. As shown in FIG. 3, this UDI information can be transferred to each individual prescription order 14 when medication from that supply container 33 is transferred to an individual prescription order 14.

For example, the supply container can include a first machine readable tag 50a that is readable by a tag reader 52 in communication with a computer system 22. A second machine readable tag 50b can be operably secured to the individual prescription order 14. The first tag 50a can include UDI information about the medication contained in the supply container 33 including the remaining volume or number of pills contained therein. When the individual prescription order 14 is filled and a portion of the contents of the supply container 33 are transferred to the container containing the individual prescription order 14, the computer system 22 can detect this activity and associate the individual prescription order 14 of that tagged individual prescription container to a customer or patent's prescription order. The computer system can transfer the resulting UDI information of the supply container 33 to the tag 50b associated with the individual prescription order 14. This UDI information from the supply container 33 travels with the individual prescription order 14 to a storage area 55 until that order is dispensed to a customer or patient. Preferably, the storage area 55 includes one or more tag readers 52 and transducers 250 in communication with the computer system 22 that operate as further described herein.

The stock supply within the stock supply container may also include one or more items related to a particular patient, or a group of items related to a particular medical treatment such as first aid treatment, cardiac treatment, burn treatment, laceration treatment, anesthesia treatment, and/or a predetermined medical procedure.

UDI Information Preserved when Medication is Returned to Stock

Referring to FIG. 4, should an individual prescription order 14 be returned to stock or the like, the system can track and store the UDI information about the returned medication, thereby allowing it to be re-dispensed without risk of it becoming expired or without knowing its exact pedigree. The computer system 22 can read the tag 50b associated with the returned prescription order 14 and the tag 50a associated with the supply container 33 and compare the UDI's of each. If key items of UDI's are identical, such as lot number, expiration date. NDC and pedigree number, the returned medication can be placed back into the supply container 33 without compromising the integrity of the supply container 33 as shown by arrow 72 in FIG. 4. The system can activate one or more transducers if the transfer of the returned medication is not authorized and alert a pharmacy worker if the UDI of the supply container 33 has been compromised.

Alternatively, if the UDI's between the returned medication and the supply container 33 do not match, the returned medication can remain within the storage area for use to fill a new prescription order as shown by arrow 74 in FIG. 4. The computer system 22 can alert a pharmacy worker whether to use medication from the returned prescription order or from the supply container.

Having described how the computer system 22 maintains and tracks UDI information from the supply containers 33 to the individual filled prescription orders 14. It can be appreciated that medication loss can be minimized by preserving UDI integrity of the returned to stock medications, and inadvertent dispensing of expired medications to customers and patents can be eliminated.

An exemplar individual prescription filling system 80 taking full advantage of maintaining medication UDI information integrity throughout the filling process is shown in FIG. 5. In step 90, a new individual prescription order is provided to the pharmacy. The pharmacy first determines if there are qualifying returned to stock medications available to fill the new prescription order (Step 92). If there is, the system next determines if there is enough of the returned to stock medication to fill the new prescription order (Step 94) and if there is the new prescription order is filled with from the returned to stock supply (Step 96). In cases where the supply of returned medication is greater than the amount dispensed to the new individual prescription order the computer system may update the volume or quantity of medication in the returned to stock supply as medication is dispensed to fill the new prescription order.

Alternatively, if there is none or not a sufficient amount of returned to stock medication to fill the new prescription order, the system directs a pharmacy worker or an automated fill system to fill the new prescription order from the main stock supply container of the prescribed medication (Step 98).

After the individual filled prescription order is filled either from an existing returned to stock supply or from the main stock supply, the computer system transfers the UDI information of the source supply to the computer readable tag associated with the individual prescription order (Step 100). More preferably, the computer system also monitors and tracks the volume or pill count in both the supply container and the volume or number of pills placed in the container of the individual prescription. For example, it consults the database associated with that customer/patient and determines the number of pills prescribed and deducts that amount from the selected supply container and adds them to the filled individual prescription order.

The filled individual prescription order is then stored for dispensing to a customer or patient (Step 102), and a clock is initiated to track how long the individual prescription order remains in the storage area. Preferably, the individual prescription is stored in an area that is in communication with the computer system 22 to automatically monitor, detect, and log user access.

As shown in Step 104, if the individual prescription order is dispensed to a patient or customer within a predetermined time, further tracking of the UDI information and location tracking of the customer's order can stop (step 106). The UDI and other information can be stored in a database for further reference or documentation as needed.

Alternatively, if the individual medication is not dispensed to a patient or customer OR within a predetermined time, the medication within the individual prescription can be returned to stock (step 112). However, because the UDI information of the supply container is preserved and transferred to each individual prescription filled, should a medication contained within a filled prescription order waiting for pick-up expire before it is picked-up by a customer or dispensed to a patient (step 110), the system can flag the discrepancy to a pharmacy worker, such as by activating a transducer on the tag associated with that prescription order, who can correct the situation before the customer seeks to pick up the medication or before it is dispensed to a patient (step 111). The computer system 22 can further prevent dispensing of an expired medication to a patient or customer by taking additional security steps such as calling for a pharmacist override before it will unlock or locate the prescription order for the pharmacy worker, or by activating an audible warning alarm or the like.

If desired, the computer system can also update the UDI information of the individual prescription order 14 and the supply container 33 with a user entered or pharmacy preselected configurable date. Preferably, this configurable date is earlier than the expiration date of the medication contained in the respective individual prescription order 14 and supply container 33, and it is selected to give a patient or customer a reasonable time to use the medication before it will expire. The previously described flagging and warning system for expired medications could also be activated upon reaching this configurable date, thereby preventing the dispensing of medications that do not have a reasonable time to be used before they expire.

Also, the electronic tracking of pedigree information of medications in the supply container also allows the pharmacy to dispense medications that are closer to their expiration dates first, and avoid dispensing medications that are too close to their expiration dates to be meaningfully used by a customer or patient before they expire. Using the oldest inventory first and avoiding disposing of expired or nearly expired medications with this system also saves money for the pharmacy.

The computer system first compares the UDI information of each individual prescription order with the UDI information of the supply container for that particular medication (step 114). If the UDI information is the same, the medication contained within the individual supply container can be returned to the supply container (step 116). The pill count or volume of medication in the individual prescription order returned to the supply container can be automatically added by the computer system to the UDI information of the supply container. Alternatively, if the UDI information between the individual prescription order differs from the UDI information of the supply container, the returned to stock medication can be stored and tracked for further use (step 118) as previously described. Of course, the worker may choose to store separately even if the UDI's match to save time.

One skilled in the relevant art will recognize that numerous variations and modifications may be made to the configurations described above. For example, if desired in step 94, if there is not a sufficient amount of medication in a returned to stock supply of medication, a pharmacy may fill only a partial amount of an individual prescription order from the returned to stock supply. If it does this, it can pull the remaining supply from the main stock of the medication supply. If it combines medication from these two sources of supply medication into one individual container, the UDI information of that container is compromised. Accordingly, the computer system will track this individual prescription order to ensure that it is not returned to stock for reuse. Alternatively, the pharmacy may provide two individual containers, each with an individual machine readable tag and each containing the UDI information of the supply source from which it was filled. In such case, the medication contained within each individual container may be returned to stock as previously described while maintaining UDI integrity of all the medications.

Also, the storage area 55 (FIG. 3) for filled prescription orders 14 needs to be spaced apart from the storage area of the supply containers. In such case, should a filled individual prescription order be flagged for being returned to stock and stored in the same area where the supply of that medication is also stored, the "return to stock" function can be purely electronic, whereby the computer system simply reclassifies that that individual prescription order as being returned to stock medication without that item actually being moved. Of course, any customer identifying labeling information would still need to be removed before the returned item could be dispensed to a new customer.

Ownership of a Customer/Patient's Medication May Transfer from the Manufacturer or Third Party Owner Directly to the Customer/Patient.

Referring to FIG. 6, the previously described individual tracking of UDI, ownership and pricing information a particular customer's 204 prescription order 14 allows ownership of a particular prescription order 14 to pass directly from the manufacturer or third party owner 200 of the medication to the customer/patient 204 upon the dispensing of the medication from a pharmacy 202 to the patent.

The previously discussed "return to stock" feature of the system allows ownership and pricing information of a particular prescription order to be preserved when a prescription order has not been timely picked up by a customer/patient, thereby maintaining ownership integrity of the prescription order.

Accordingly, it can be appreciated that the pharmacy may maintain a supply 33 of a medication while the manufacturer or third party owner 200 of that medication maintains ownership of it until it is dispensed to a customer/patient. This prevents the pharmacy from having to purchase and then resell a particular medication that it stocks. Instead, a manufacturer may supply pharmacies with high cost medications to dispense without the pharmacy incurring the financial burden of pre-paying for the supply of medication before it is ordered or dispensed to a customer/patient. The sale of individual prescription orders from that supply of medication triggers the transfer of ownership of that prescription order's medication to the customer and payment of that medication of the manufacturer or third party owner of the medication.

In cases where a customer has insurance 300 to pay for a particular medication, the system can monitor the status of the insurance transaction between the pharmacy and patent, and temporarily transfer ownership of a particular medication to the insurer. This is usually performed when an insurer as paid for a medication on behalf of a customer, but the customer has not yet fulfilled any obligations under the insurance agreement such as pay a co-pay to the pharmacy or the like. In such case, the owner of that particular medication would be transferred from the manufacturer or third party owner to the insurance company until the contractual obligations of the customer have been satisfied and the medication is dispensed to the customer. The insurer and pharmacy can establish a protocol for returning ownership back to the manufacturer or third party owner should the customer fail to pick up the prescription order within a predetermined period. Thereby, allowing ownership of the prescription order to transfer back to the manufacturer or third-party owner without it ever being owned by the pharmacy.

The foregoing description of embodiments has been provided for purposes of illustration and description. It is not intended to be exhaustive or to limit the disclosure. Individual elements or features of a particular embodiment are generally not limited to that particular embodiment, but where applicable, are interchangeable and can be used in a selected embodiment, even if not specifically shown or described. The same may also be varied in many ways. Such variations are not to be regarded as a departure from the disclosure and all such modification are intended to be included within the scope of the disclosure.

Additional Possible Security Features

Referring to FIG. 7, it can be appreciated that the information stored in and collected by computer system 22 in communication with the tags 50 installed on the supply containers 33, individual filled prescription orders 14 and the workers 150 within the pharmacy can be used to provide a wide variety of security features. For example, it can be used to ensure the proper dispensing of medications, minimize required storage space, quickly identify status changed medications within the system, and identify fraudulent, excessive or otherwise improper dispensing of medications. Examples of these types of security measures are provided below.

Fraud Module

The computer system 22 can be equipped with a fraud module 302, which may be software provided in the system, that evaluates the collected UDI data associated with filling a prescription order 14 and alerts one or more key employees with an alerting system if a predetermined discrepancy is detected. For example, because the collected data includes and stores the identity of each worker 51, 352, 354 who has had access to a particular supply container 33 of a medication, it can monitor how much of a particular medication is being dispensed by each worker within the pharmacy. If a particular worker dispenses an unusually large amount of a particular medication, the fraud module 302 can activate the alerting system 308 to alert the management or other key employees of the discrepancy.

If desired, the system can "lock out" that employee from gaining future access to that supply of medication or even all medications until the discrepancy is cleared by the key employee or management.

The predetermined criteria for the fraud module to activate the alerting system can be preset amounts of a particular medication dispensed within a certain amount of time by one worker or by all workers within the pharmacy. The preset amounts can be manually entered by the key employee or management through an input device 304 in communication with the system.

In addition and/or alternatively, the system 22 can monitor the dispensing rates of medications over a predetermined timeframe to establish historical consumption data and activate the alerting system 308 when the dispensing of a particular medication exceeds this historical data by a predetermined amount. For example, if the system determines that the pharmacy usually dispenses 100 units of a particular medication per day, it can activate the alerting system if it detects that 125 or more units have been dispensed in a day. This tracking can be covert, in that the pharmacy workers dispensing the medications do not know they are being monitored for this activity, or overt, where the workers know this tracking exists thereby deterring them from engaging in these types of improper dispensing activities.

The activating of this system doesn't necessarily mean a medication has been improperly dispensed or a particular worker has committed fraud. The system just alerts management of this discrepancy in real-time to allow management the opportunity to investigate the issue and correct it or override the alert as needed.

Medication Status Change Detection

A status change module 310 in communication with the computer system may also be provided. On occasion, the dispensing status of a medication may change. For example, a particular supply of medication from the manufacturer may be found contaminated or otherwise unsuitable for dispensing. In such case, the manufacturer will issue a recall notice to pharmacies. That notice will typically be limited to a medications with a specific UDI lot number or the like.

Because the present pharmacy tracking system monitors and tracks specific UDI information of medications all the way through to the individual filled prescription orders, the status change module 310 can automatically detect and identify any medications subject to a recall or the like. For example, if a particular lot number of a particular medication is recalled, the status change module can enter that lot number and medication name into the system to activate transducers 250 associated with all affected medications within the system.

This includes both affected medications still within supply containers 33 and those already dispensed and awaiting pick-up as filled prescription orders 14. Accordingly, should the pharmacy fail to promptly remove an affected medication, the system can alert or prevent a worker from dispensing a particular affected medication. Also, the UDI expiration of the supply of medication can be automatically monitored by the system. If a medication becomes expired while stored in the system, the system can automatically identify that supply of medication for removal from the system and prevent its dispensing to customers or patients.

The status change module 310 can receive notice of medications subject to a status change from a variety of sources. A worker 51 can manually enter medication and lot numbers into the system through the input/output device 304 in communication with the system. Alternatively or in addition, the status change module can be in continuous communication with an auxiliary source such as a national medication recall database or databases provided by the medication manufacturers thereby providing real-time notice and response to quickly prevent dispensing of affected medications.

In addition, the alerting system 308 can include customer or patient contact information such as their phone numbers, email addresses and/or their mailing addresses. In cases where the computer system 22 detects that an affected medication has already been dispensed to a customer or patient, the alerting system can be activated to notify that customer or patient as soon as possible by common means such as sending an email, text message or causing a pharmacy worker to call the customer or patient with this information.

Dual Use Storage Area

In order to maximize available storage space, the storage area 55 may be a storage compartment or cabinet 57 that is adapted to hold both supply containers 33 and filled prescription orders 14 within it, but without compromising security or providing unauthorized access of either product. As best shown in FIG. 7, the cabinet 57 can have limited access and a security system that limits that access. For example, the storage area in the compartment can be inside a lockable drawer 202. A plurality of independently operably lockable drawers may be provided in the same frame. The lock for that drawer is in communication with the computer system 22, and opened by the computer system only when it detects and verifies the identity of a particular worker who is seeking access to a supply container or filled prescription order received therein.

The compartment includes one or more tag readers 52 that automatically detect the presence of tags 50 on both supply containers 33 and filled prescription orders 14 within the system. It can activate transducers 250 on both the exterior of the cabinet drawer and on the shelf adjacent to the supply container 33 or filled prescription order 14. Thereby alerting a particular worker 354 to the exact location where the desired supply container 33 or filled prescription order 14 is located.

Moreover, the system 22 can detect the removal of a supply container or filled prescription order from the compartment and compare the removed item against the desired item being sought by the worker 354. Should a worker inadvertently select the wrong item from the cabinet, the alerting system 308 will alert the worker 354 and management 352 of the discrepancy. Accordingly, pharmacy workers filling prescription orders from supply containers 333 and those dispensing filled prescription orders 14 to customers and patients may use the same storage compartment 57 while maintaining control of items received therein.

Preferably, the identity of each worker 51, 354 accessing the compartment is determined from a tag 50 worn or held by the worker. That tag is preferably an RFID tag, but alternative machine readable tags could be used including bar codes or the like. Alternative forms of identification of the worker can be used too. For example, keypad entry and/or biometric data such as fingerprint detectors and/or retinal eye scanners and the like could be used.

It can be appreciated that the preferred system 22 monitors and tracks the real-time location of supply containers and filled prescription orders by tag readers detecting the physical location of these items at predetermined locations within the pharmacy. Accordingly, the computer system updates its database with this information in response to the worker's choice as to where to put a particular item rather than the system first telling a worker where to put an item and assuming that worker has actually complied with that instruction. This allows supply containers 33 and filled prescription orders 14 to be placed anywhere within the pharmacy and in the storage compartment and still be easily located as needed.

Receive Module

This real-time updating of the compiled database of UDI, worker access identification, physical location of the item, customer identification and the like can be used to provide a wide variety of other benefits. For example, a real-time manifest of current medications with the pharmacy can be provided. A receive module 306 may be provided to the system 22 that allows a supply shipment received by the pharmacy to be instantly compared to a manifest to determine if any discrepancies exist. In one embodiment, the contents of a supply shipment may include numerous supply containers of different medications. At the pharmacy, each supply container within the shipment may be assigned an individual tag and the UDI information, including quantity, associated with the medication contained in the respective supply container is associated with the tag 50. The receive module 306 can compare the original manifest of the supply shipment with the individual tags associated with each individual supply container and note any discrepancies between the manifest and the tagged individual supply containers. This minimizes risk of items received within a bulk supply shipment from inadvertently or intentionally failing to be entered into the system by a worker upon receipt at the pharmacy. If the received quantity matches the manifest quantity for that freight order then the system can automatically "increment" the real-time inventory of the system.

Real-Time Inventory Module

Similarly, a real-time inventory module 312 may be provided that uses the collected data and tracking of the system allow for the system 22 to provide a real-time inventory of available supply containers and their medications stored therein. The inventory module 312 may include an input-output device 304 that allows pharmacy workers to request inventory information, and/or predetermined minimums may be entered into the system to alert the pharmacy workers should a particular medication fall below a predetermined minimum amount. If desired, the system can be provided to automatically re-order supplies that fall below these predetermined limits. Alternatively or in addition, a real-time and accurate report can be generated and logged to comply with physical count requirements of national, state and/or local authorities and laws.

Perpetual Log/Blind Back Count

The collected data and tracking system may also be used to create and maintain a perpetual data log of key transactions and processes. For example, in one embodiment when a pharmacy worker may decide to fill a prescription order, he or she can scan a prescription barcode on the label attached to the prescription order. The computer system knows the UDI's, such as National Drug Code (NDC), and the quantity of the desired medication to be filled with that prescription order.

The computer system 22 can compare the prescription order's NDC to what is available in supply containers in the cabinet, and if there is an exact match, it can direct them to one or more supply containers with that NDC and to enough quantity as more than one supply container may be needed. Preferably, the system would direct the worker to the oldest matching NDC first plus any returned to stock product with matching UDI's.

In one embodiment, the system 22 can alert the worker 354 by activating transducers 250 such as lights positioned on the exterior and interior portions of the cabinet adjacent to the desired supply container(s). The lights on the cabinet drawer lights up where the desired supply containers are located. When the worker identifies themselves to the computer system at the identified drawer, the lock will unlock and the known user can access/open the drawer. Then, the cell or cells lights up with the desired supply containers. This way the system can electronically verify that the correct UDI is picked. The system logs accuracy and accountability. Once the worker retrieves the basket with the supply container and closes the drawer the supply container is "checked out" to that worker.

Since the system knows what prescription order this transaction was for, and the system also knows the quantity of the medication to the removed from the supply container to fill that prescription order, the system automatically, decrements and stores in memory that number from collected data of the supply container used to the fill the prescription order. Accordingly, the system uses this information to maintain a current log of the quantity of medication remaining in the supply container used to fill the prescription order.

If desired, the system 22 can require the worker 51 to manually count the remaining medication in the supply container used to fill the prescription order and manually enter that quantity into the system though a user interface. If the quantity manually entered by the worker matches the system's self-maintained current log of quantity of medication remaining in that supply container then the system will authorize that worker to return that supply container to the cabinet. This process is referred to as a "blind back count." Upon the system authorizing the return of the supply container, the system can unlock the cabinet upon determining the identity of the worker seeking entry and remove the "check-out" of that supply container to the worker, and verify that the supply container has indeed been returned to the cabinet.

If the system 22 determines there is a discrepancy, the worker must have a pharmacist or other authorized management personnel with higher authority adjust the inventory in the system so that the manual count matches the system's count, and the user can then put the supply container back into the cabinet as previously described. The system can therefore identify which workers are historically requiring an inventory adjustment and thereby prevent and/or monitor for fraudulent transactions by those workers.

In this case, the worker 51 who had the supply container "checked-out.", the manager 352 who adjusted the inventory and any workers 354 who accessed (put away) the supply container 33 previously to this transaction is logged and an exception is created that must be reviewed by the manager 352. The manager's review is also logged.

Also, since the system 22 knows there was a prescription order 14 filled with this transaction, the system 22 can also look to see if a tag 50 associated with the filled prescription order 14 is linked (coupled) to the transaction and alert a worker 362 if the filled prescription order is not promptly located and accounted for by the system. The filled prescription order 14 may be returned to the same cabinet as the supply container 33 thereby maximizing available storage space within the pharmacy.

Also, the system can mandate that this linked prescription order be checked by an additional worker such as a pharmacist before it goes into the cabinet. The system does this by requiring a "double count" where the additional worker double counts what is in the filled prescription order's vial, enters this into the system and if it matches, is authorized to put this filled prescription order into the cabinet(s) for customer pick up later. Should another (non-pharmacist or user without privilege) put this basket into the cabinet, the system will generate an error and alert the pharmacy workers.

Also, if desired the system 22 can have a sense of "roles" within the pharmacy. It can be equipped to provide increasing access privileges to the cabinet based on the roll assigned to each worker. For example, a technician 51 may be allowed to access supply containers 33, including stock storage containers and the like, but a clerk 354 may only be able to access a filled prescription order 14. Because the system monitors and tracks the identify of each worker gaining access to the cabinet, and can differentiated between supply containers 33 and filled prescription orders 14 within it, it can be provided with predetermined rules to limit access to particular items within the system.

Preferably, to maintain the chain of custody, the system would verify that the person doing the last count (double count) be the same person to put away into our cabinet. If not, the system can generate an error and alert the pharmacy workers.

Also, the last worker to have touched a particular supply container, bulk shipment or filled prescription order can be determined, and the amount of time it takes a particular pharmacy worker to perform a particular task can be determined. The data contained in this database can be stored indefinitely for future reference and analysis as needed, thereby improving accountability.

One skilled in the relevant art will recognize that numerous variations and modifications may be made to the configurations described above. For example, not all of the security features noted herein need be included in a commercial embodiment. Such modifications and additional embodiments can be made without departing from the scope of the present invention, as defined by the appended claims.

I claim:
1. A pharmacy system comprising:
a computer system;
a tag reader in communication with the computer system and configured to wirelessly detect a presence of respective tags;
a database in communication with the computer system and storing at least one unique identifier associated with a stock supply of an item contained in a stock container,
the computer system configured to:
  detect, using the tag reader, that a first machine readable tag associated with a patient prescription container is within a proximate location of a second machine readable tag associated with the stock container when a portion of the stock supply of an item is dispensed from the stock container to patient prescription container; and
  automatically associating, based on the detecting, the at least one unique identifier with the portion of the stock supply of the item placed in the patient prescription container; and,
a security system in communication with the computer system having a security module configured to detect a predetermined discrepancy associated with the portion of the stock supply being dispensed from the stock container.

2. The pharmacy system of claim 1, wherein the stock supply of an item is a unit of use.

3. The pharmacy system of claim 1, wherein the stock supply of an item contains a plurality of items and each of the plurality of items is associated with a same common group.

4. The pharmacy system of claim 3, wherein the common group is a patient, and the plurality of items are a plurality of medications for that patient.

5. The pharmacy system of claim 3, wherein the common group is a collection of items used to treat a particular medical condition.

6. The pharmacy system of claim 5, wherein the particular medical condition is selected from the group consisting of first aid treatment, cardiac treatment, burn treatment, laceration treatment, anesthesia treatment, and a predetermined medical procedure.

7. The pharmacy system of claim 1, further including:
a worker identification system in communication with the computer system for individually identifying workers within the pharmacy; and,
wherein the security system is a storage area having a tag reader in communication with the computer system thereby allowing the computer to detect the identity of the worker accessing one of the stock containers within the storage area.

8. The pharmacy system of claim 1, wherein the security system comprises a cabinet for storing patient prescription containers and stock containers including the stock container therein, the cabinet comprising:
a frame defining a storage area therein;
an access panel having an open position wherein the storage area is accessible to a worker and a closed position wherein the storage area is inaccessible to a worker;
at least one transducer operably secured to the cabinet operable by the computer system to alert a worker as to the location of the patient prescription container within the cabinet; and,
a worker identification system in communication with the computer system for limiting access to the storage area to a specifically identified worker by selectively activating the transducer based on the identity of the worker.

9. The pharmacy system of claim 1, wherein the security system includes a cabinet for storing stock containers therein, the cabinet having:
- a frame defining a storage area therein;
- an access panel having an open position wherein the storage area is accessible to a worker and a closed position wherein the storage area is inaccessible to a worker;
- a lock in communication with the computer system that is activated by the computer system based on predetermined criteria; and,
- a worker identification system in communication with the computer system for limiting access to the storage area to a specifically identified worker by the computer system selectively activating the lock on the access panel.

10. The pharmacy system of claim 9, wherein the worker identification system is a machine readable tag operably secured to the worker.

11. The pharmacy system of claim 10, wherein the machine readable tag is selected from the group consisting of a Radio Frequency Identification Tag and a biometric reader.

12. The pharmacy system of claim 11, further including a plurality of access panels, each panel having a panel lock in communication with the computer system, each panel lock independently activated by the computer system based on predetermined criteria.

13. The pharmacy system of claim 12, wherein the predetermined criteria provides that the lock to at least one of the access panels is unlocked only for storing a stock container within the storage area.

14. The pharmacy system of claim 9, wherein the computer system maintains a perpetual log of a worker's identity and contents of the stock container within the cabinet for said worker.

15. The pharmacy system of claim 12, wherein the computer system automatically assigns possession of the stock container upon that worker removing the stock container order from the storage area.

16. The pharmacy system of claim 1, wherein the computer system maintains a perpetual log of a unique identifier (UI) associated with a stock container and associates that UI with a customer who has been provided an item from the stock container.

17. The pharmacy system of claim 1, wherein the security system is a status change module for automatically changing a status of items within the system subject to a status change.

18. The pharmacy system of claim 1, wherein the security system is an automatic real-time inventory module for generating real-time inventory reporting of items received within the pharmacy.

19. The pharmacy system of claim 18, wherein the security system includes providing notice to a worker that a quantity of an item within a supply container has dropped below a predetermined threshold and needs to be replenished.

20. The pharmacy system of claim 1, wherein the security system is a receive module for providing real-time discrepancy monitoring and notification of bulk supplies entered into the system as supply containers by the computer system automatically comparing a manifest of the supplies with tags associated with one or more supply containers containing products from that manifest.

* * * * *